Nov. 12, 1963 H. C. BROWNELL Plant Pat. 2,304
ROSE PLANT
Filed Sept. 5, 1962
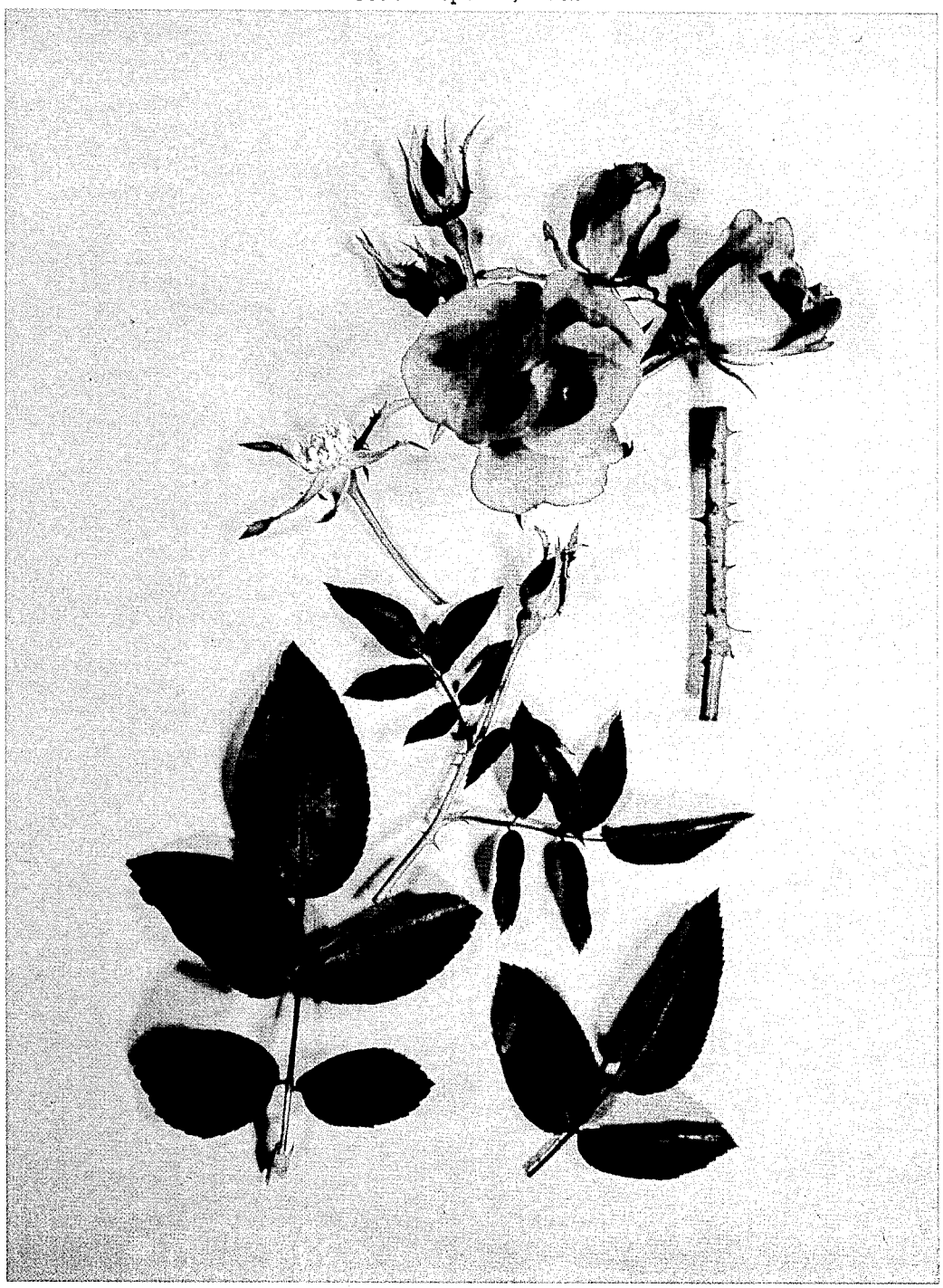
Inventor
Herbert C Brownell United States Patent Office Plant Pat. 2,304
Patented Nov. 12, 1963

2,304
ROSE PLANT
Herbert C. Brownell, Little Compton, R.I.
Filed Sept. 5, 1962, Ser. No. 221,639
1 Claim. (Cl. Plt.—28)

My invention relates to rose plants and especially to a new, original and distinct variety of the class known commercially as "floribunda" and is a variant in that class, being a *Rosa wichuraiana* hybrid tea hybrid, produced by me and under my direction in the breeding grounds of my research gardens in Little Compton, Rhode Island, by cross pollination, which can be and has been asexually reproduced.

My new rose is new as to the following characteristics and especially as to their joint association with the characteristics inherited from *Rosa wichuraiana*, of hardiness, or immunity from serious injury on account of cold temperatures prevailing in certain parts of the Northern United States;

The red shades (ordinary dictionary definition) of its petals, in combination with the unique brilliance thereof and their tendency to hold this color under exposure;

The novelty and variation within certain definite limits of the form of the bloom, its character of holding that form for a long time, and the petalage of the flowers;

Its character of fragrance;

Its unusual abundance of flowers, in clusters, notably after early bloom time until frost;

The intensity of its remontant and everblooming or reblooming character;

Its character of ascending in height by recurrent branching and progressively longer stems from the base in some instances long enough to be classified as canes;

The character of producing many seven-leafleted leaves; which character seldom has obtained on hybrids not having *Rosa wichuraiana* ancestry, but frequently obtains on flower stems of descendants of *Rosa wichuraiana* of the dwarf reblooming type.

In the accompanying photographs forming a part of this specification I have shown my new rose in its natural colors, that is, as near as is possible to do so photographically.

My new rose is otherwise described as follows:

*Essential Information*

Color terminology in accordance with the Horticultural Color Chart of the British Color Council, except where general terms of ordinary dictionary significance are obvious:

Type: Floribunda, *Rosa wichuraiana* hybrid, hardy; outdoor; seedling; for cut flowers and for garden decoration.

Class: Floribunda, further restricted by originator to include only those varieties that can survive moderately low sub-zero temperatures.

Breeding: This variety was produced and bred by me and under my direction by propagation and cross-pollination.

*Seed parent.*—Floribunda-type rose not patented but commercially known as "Nearly Wild."

*Pollen parent.*—A known but unnamed hybrid tea seedling.

The plant and flower seemed to me to be of unusual merit and I have since made and directed extensive propagations and tests thereof.

Plants of this variety budded from this seedling on to *Rosa multiflora* root stock, have after being exposed to moderate sub-zero temperatures, survived and bloomed normally the following season in the floribunda manner. The variety has been propagated by budding at Little Compton, Rhode Island, and the characters have successively reproduced, true to the original seedling.

*Flower*

Habit: It blooms out of doors in Little Compton, Rhode Island about one week prior to the average beginning time of commercial hybrid teas and continues relative of the growth of the plant until frost.

Flowers borne: Several to ten or fifteen to stem on stems of medium length to stems occasionally three feet in length in clusters.

Quantity of bloom: Abundant, outdoors.

Continuity: Continuous.

Fragrance: Slight. Tea.

Bud:

*Peduncle.* — Medium; medium caliper. Willow Green 000862/1.

*Before calyx breaks.*—The size is medium, form pointed, sepals extending beyond the apex of the calyx up to about one quarter of an inch.

*As calyx breaks.*—Color of bud is Indian Lake 826.

Bloom:

*Size (when fully open).*—Small from 1½ inches to 2 inches.

*Petalage.*—Single; five petals.

*Form.*—Cupped at first, but becoming open cupped; petals being at first flat and remaining flat at maturity.

*As first petal opens.*—Color is Tyrian Purple 727/1 on inside of petals and Rose Red 724 on outside of petals.

The petals are substantial in texture, medium to thick and after about five or six days, drop off cleanly, except that occasionally a single petal or petaloid will cling to drop off later.

Reproductive organs:

*Stamens.*—Abundant of uneven length.

*Anthers.*—Majolica Yellow 09.

*Pistils.*—Variable in length and quantity.

*Ovaries.*—Usually all enclosed.

*Hips.*—Globular; color same as underside of leaves turning to a rust brown (ordinary dictionary definition) when matured.

*Sepals.*—Generally five in number.

*Seeds.*—Variable; ten to twelve in each hip.

*Plant*

Foliage:

*Leaves.*—Compound of five and sometimes seven leaflets; normal abundance, medium, size, glossy.

*Leaflets.*—Shape—variable ovate—cuspidate to ovate lanceolate.

*Color.*—Mature: upper surface—Parsley Green 00962; under surface—Sage Green 00861.

*Rachis (the supporting stem of the compound leaf).*—Medium caliper. Upper side—grooved, hairy. Under side—sparsely prickly.

*Stipules.*—Medium length and width; with points of medium length turning out at an angle of about 45°.

*Disease resistance.*—Comparable to that of the average variety grown under the same cultural conditions at Little Compton, Rhode Island, U.S.A.

Growth:

*Habit.*—Bushy; much-branched.

*Growth.*—Vigorous.

*Canes.*—Medium caliper.

*Main stems.*—Bright. Color—Spinach Green 0960/3. Prickles—several; color—Pod Green 061/2, overlaid with Cardinal Red 822/3.

*New growth.*—Bright. Color—Lettuce Green 861/1.

I claim:

A new distinct variety of rose plant of the floribunda class, substantially as herein shown and described, characterized particularly as to its habit of growth by branching, its prolific bloom quantity in clusters and its characteristics that make it an ideal bedding or hedge plant, characterized by its unique color arrangement, bloom cluster and resistance to moderate sub-zero temperatures.

No references cited.